United States Patent [19]

Ulutin

[11] Patent Number: 5,081,109
[45] Date of Patent: Jan. 14, 1992

[54] PHARMACEUTICAL COMPOSITION AND METHOD FOR THE THERAPY OF PERIPHERAL ARTERIOPATHIES

[75] Inventor: Orhan N. Ulutin, Istanbul, Turkey

[73] Assignee: Crinos Industria Farmacobiologica Spa, Villa Guardia Como, Italy

[21] Appl. No.: 218,514

[22] Filed: Jul. 5, 1988

Related U.S. Application Data

[63] Continuation of Ser. No. 96,282, Sep. 14, 1987, abandoned, which is a continuation of Ser. No. 649,055, Sep. 10, 1984, abandoned.

[30] Foreign Application Priority Data

Sep. 12, 1983 [IT] Italy .............................. 22855 A/83

[51] Int. Cl.$^5$ .............................................. A61K 27/00
[52] U.S. Cl. ..................................... 514/44; 514/824; 536/24; 536/28; 536/27
[58] Field of Search ................... 514/824, 44; 536/27, 536/28, 29, 24

[56] References Cited

U.S. PATENT DOCUMENTS

| | | | |
|---|---|---|---|
| 3,770,720 | 11/1973 | Butti et al. | 536/24 |
| 3,829,567 | 8/1974 | Butti et al. | 424/180 |
| 3,899,481 | 8/1975 | Butti et al. | 536/28 |
| 4,309,364 | 1/1982 | Bentzen et al. | 514/866 |
| 4,351,950 | 9/1982 | Sircar | 514/824 |
| 4,366,161 | 12/1982 | Mori et al. | 514/824 |
| 4,416,877 | 11/1983 | Bentzen et al. | 514/824 |
| 4,450,272 | 5/1984 | Du et al. | 514/824 |
| 4,485,105 | 11/1984 | Shephard | 514/824 |
| 4,614,744 | 9/1986 | Bellani et al. | 514/277 |
| 4,649,134 | 3/1987 | Bonomini | 514/44 |
| 4,693,995 | 9/1987 | Prino et al. | 514/44 |

OTHER PUBLICATIONS

Ulutin et al., Abstract No. 107, VIII International Congress on Thrombosis, Istanbul, Turkey, Jun. 4–7, 1984.
Gelister et al., Abstract No. 108, VIII International Congress on Thrombosis, Istanbul, Turkey, Jun. 4–7, 1984.
Pescador et al., Pharmacokinetics of Defibrotide and of Hs Profibrinolytic Activity in the Rabbit, Thrombosis Research 30, 1–11 (1983).
Abstract No. 1162, Thrombosis and Hemostasis 42, 4747 (1979).
Modern Drug Encyclopedia, pp. 871–873, 973 and 974 MDE/16.
Pharmacological Basis of Therapeutics, pp. 1360–1362 (Sixth Ed.), MacMillan Publishing Co., Inc.
Thrombosis, Haemostas (Abstr. VIIth Internat. Cong. Jul. 1979), No. 1162.
Haemostasis, Mar. 1984 (7th Internat. Cong. on Fibrinolipis), Abstracts 226, 227 and 228.

*Primary Examiner*—Ronald W. Griffin
*Attorney, Agent, or Firm*—Armstrong, Nikaido, Marmelstein, Kubovcik & Murray

[57] ABSTRACT

The use of pharmaceutical compositions containing as the active ingredient Defibrotide permits peripheral arteriopathies in advanced phase (phase III and IV) to be treated by a therapeutical route.

10 Claims, No Drawings

PHARMACEUTICAL COMPOSITION AND METHOD FOR THE THERAPY OF PERIPHERAL ARTERIOPATHIES

This application is a continuation of application Ser. No. 096,282 filed Sept. 14, 1987, now abandoned, which is a continuation of application Ser. No. 649,055 filed Sept. 10, 1984, now abandoned.

The present invention relates to a pharmaceutical composition useful in the medical therapy of peripheral arteriopathies, particularly those in phases III and IV of the Fontaine classification.

The problem of the prevention and therapy of the obliterating arteriopathies of limbs has today an increasing importance owing to the constant increase of the patogenecity and mortality related to such a pathology in all the industrialized countries. The epidemiological studies have revealed that the most involved age is that of between 45 and 70 with a relevant increase from 45 to 60. The instauration of a "turbulent" blood flow, as it occurs in the presence of an atherosclerotic plate onto the surface of a vasal wall, causes a constant traumatic action against the surface of the involved vessel, which is essentially manifested by the proliferation and thickening of the intima and through the modification of the endothelial permeability. The platelets adhere to and aggregate onto the wound endothelium, thus starting a process of maintaining and worsening the atherosclerotic lesion in itself. Consequently the atherosclerotic plate tends to gradually extend with the unvoidable and consequent formation of an occlusive stenosis of the involved arteria.

The patients affected by peripheral arteriopathies have frequently to face a thrombotic evolution of the stenosating lesion with a complete occlusion of the a vasal port and with a sometimes dramatic worsening of the simptomatology. In an area affected by a stenosis caused from an atherosclerotic plate wherein relevant emodynamic changes occur, there can be furthermore generated localized variations of the coagulating omeostasis. The presence of a thrombophilic state, in such a case, can be considered as the factor responsible of the thrombotic phenomenum.

Since the basic therapeutical problem (the atherosclerotic disease) is a problem of preventive medicine, the treatment must be directed as a matter of principle to the district manifestations of the disease, among which the peripheral arteropathies represent one of the more significant and more frequent forms. According to the Fontaine classification the evolution of arteropathies takes place by phases. To date it is acknowledged that the first two steps, characterized by a reduction of the working capacity of the affected limb, are mostly of medical interest.

The last two phases (III and IV), characterized by pain at rest and by trophic alterations, are actually of exclusive surgical interest. The medical therapy intervenes as an auxiliary aid, mainly by means of analgesics, since in these phases, according to most of bibliographic sources, such a therapy does not provide results which can be appreciated under the prognostical profile. In the forms of arteriopathies in the phase III and IV no efficacious medical therapy has been to date codified. However some therapeutical approaches have been suggested which can be resumed as follows:

1) The use of peripheral vasodilators has been proposed, such as nicotinic acid and derivatives thereof and flunarizine.

Although the theoretical assumption seems to be convincing, a practical confirmation lacks since the effects thereof must take place with respect to already sclerotized vessels. Moreover, in pathological conditions, the vasodilating drugs have a more relevant effect on the heslty districts rather then on the ischemic ones: consequently they can be the cause of the so called "ematic rubbery" just in those areas in which the need of an adequate vasal irroration might be greater.

Side effect:

flush, nausea and vomiting, headache and giddiness, rarely orthostatic hypotension and tachycardia.

2) The use of platelet antiaggregating drugs has been proposed, such as dipiridamol, sulfinpyrazone, acetyl salycilic acid, ticlopidine. Their specific action is that of preventing a further evolution of the thrombus and prevent later thrombotic occurrences. However they cause several side effects mainly during extended therapies (gastrointestinal disturbances, blooding risks) and other effects sometimes related to the intrinsic properties of the subject substances.

3) Another approach consists in the administration of drugs, such as for instance pentoxiphylline, adapted to improve the rheological properties of the blood. Often these properties are altered in the arteriopathic patient. The increase of the rigidity of the erytrocite wall, together with other plasmatic factors (fibrinogenemy), may cause an increase of blood viscosity.

The results of the clinic experimentation carried out with these drugs do not permit univocal conclusions to be drawn from the therapeutical point of view. Moreover substances are involved which may cause frequent side effects (sonnolence, cutaneous flush, orthostatic hypotension, etc.)

4) A further type of approach consists in the administration of the so called major fibrinolytic agents, such as for instance urokinase and streptokinase. They are indicated in the upper arterial occlusions (aorta bifurcation, iliae arteriae, first lenght of the femoral arteria) especially in the patients which can not undergo a surgical intervention.

The percent of success which can be obtained with such a therapy mainly depends on how prompt is the intervention with respect to the time of the occlusion occurrence and with respect to the position of the same. A certain improvement of the pain and the delimitation of the trophic lesions is found after an extended administration of urokinase, which however must be used with extreme caution owing to the high risk of haemorrhagies.

It has been now found and is the subject of the present invention that the administration to patients affected by peripheral arteriopathies, particularly obliterating arteriopathies of the limbs, in the phase III and IV, of pharmaceutical composition the active ingredient of which consists of defibrotide, permits the simptomatological frame and its evolution to be controlled, without need of surgical intervention.

More specifically the present invention is thus concreted in a pharmaceutical composition for the medical therapy of peripheral arteriopathies which is characterized by containing, as active ingredient, defibrotide, namely the polyanionic sodium salt of necleotidic fractions (polydesoxyribonucleotides) with low molecular weight.

The defibrotide (DCI, liste 21, Chronique OMS, 35, suppl. 4, 1981) is a polydesoxyribonocleotide (U.S. Pat. No. 3,829,567), obtained by extraction from animal organs (see U.S. Pat. Nos. 3,770,720 and 3,899,481 which are herein referred to for more details), devoid of anticoagulating activity and of haemodynamic effects and which shows relevant profibrinolytic and antithrombotic activity under a number of experimental conditions "(Anti-thrombotic activity of polydeoxyribonucleotides of mammalian origin (Laboratory code: Fraction P.) in experimental animals". VII International Congress on Thrombosis and Haemostasis (London, 15-20 July 1979) Abs. No. 1162, Thrombosis and Haemostasis, 42, 4747, 1979 and Pescador R. et al. "Pharmacokinetics of Defibrotide and of its profibrinolytic activity in the rabbit". Thrombosis Research, 30, 1-11, 1983).

However the fact that the administration in the case of peripheral arteriopathies (particularly obliterating arteriopathies of the limbs among which also the Buerger disease) of other drugs known for their fibrinolytic and/or antithrombotic activity, which had no satisfactory results in the phase III and IV, apart from modest temporary improvements, would have consequently induced to exclude the use of the defibrotide in these cases, whereby the thus achieved therapeutical results appear to be even more surprising.

The abovementioned U.S. Pat. Nos. 3,829,567; 3,770,720 and 3,899,481 are hereby incorporated by reference for the disclosure of defibrotide and methods of preparation thereof disclosed therein.

The confirmation of the therapeutical efficacy of the pharmaceutical composition of the invention has been given by clinical experiments carried out in patients in a period of about 18 months. The patients have been hospitalized with a diagnosis of obliterating peripheral vasculopathy (atherosclerosis or Buerger disease) and were treated for 7-10 days with daily dosages of 600 mg of defibrotide administered by intravenous route (in 15 minutes). Subsequently the administration was continued for 3 months with the defibrotide being administrated two times each week. The patients were divided in two groups, the first of which (26 patients comprising 24 men, and 2 women, 5 of which were diabetic) was affected by atherosclerosis, with an average age of 56.5.

The second group (consisting of 8 men) was affected by Buerger disease with an average age of 28.5.

In seven of eight patients of the second group it was assessed:
  disappearance of the pain at rest;
  increase in a short time of the distance which might be covered without pain;
  resolution of the ischemic ulcerating lesions within two-three weeks;
  a significant increase shown by arteriographic examination of the blood flow through the limbs, this improvement still holding one-three months after the interruption of the treatment.

For the patients of the first group, affected by atherosclerosis, after an initial worsening of the pain it was assessed:
  total disappearance of the pain of the limbs at rest;
  feeling of warmth of the limbs;
  increase of the distance which can be covered without pain;
  disappearance or definite improvement of the ulcerating lesions of the ends of the limbs (even in diabetic patients).
  increase of the blood flow to the limbs (as shown by the arteriographic examination).

Since the defibrotide, as confirmed by the number of publicated papers, is practically devoid of toxicity and at the same time devoid of unfavourable side effects, it consequently permits an extended administration, both for therapuetical purpose and for the maintaining of the results achieved in the acute phase. The amount of defibrotide to be administered to a given patient will vary according to the specific conditions involved, including the specific conditions of obliterating peripheral arteriopathies, as well as the size and general health of the patient. Normally a daily dosage of defibrotide in the range of 400 to 800 mg will be used for an adult patient, generally corresponding to a daily dosage of about 6 to 12 mg per kg of body weight.

The pharmaceutical compositions according to the invention may be prepared both in oral form (capsules, tablets, etc.) and in injectable form (vials for intramuscular and intravenous use), by the known pharmaceutical techniques, with the common excipients, vehicles, solvents, etc. The pharmaceutical compositions of the present invention are usually prepared following conventional methods for administration in a pharmaceutically suitable form. Compositions in the form of solid oral forms may contain in addition to the active compounds diluents such as lactose, dextrose, saccarose and other sugars, cellulose, mais, starch and other vegetable starches such as corn starch and potato starch, lubricants such as silica, talc, stearic acid, magnesium or calcium stearate and/or polyethylene glycols, binding agents such as vegetable starches, arabic gums, gelatin, methylcellulose, carboxymethyl cellulose, polyvinyl pyrrolidone, and the like, disaggregating agents such as starch, alginic acid, alginates, sodium starch glycolate, and in general non-toxic and pharmacologically inactive substances commonly used in pharmaceutical formulations. The solutions for intravenous injections or infusions may contain as a carrier sterile water or preferably sterile aqueous isotonic saline solutions.

EXAMPLE 1

Pharmaceutical composition for injectable use: 2.5 ml vials

| | |
|---|---|
| defibrotide | mg 200 |
| trisodium citrate dihydrate | mg 25 |
| metil p-hydroxybenzoate | mg 3,13 |
| propil p-hydroxybenzoate | mg 0.62 |
| water for injectable preparations enough to | mg 2.5 |

EXAMPLE 2

Pharmaceutical composition for oral use

| Capsules (content) | | | |
|---|---|---|---|
| defibrotide | 200 | 100 | 50 |
| lactose | 56.75 | 87.6 | 137.6 |
| colloidal silica | 0.65 | 0.5 | 0.5 |
| magnesium stearate | 2.64 | 1.9 | 1.9 |
| Tablets | | | |
| defibrotide | 200 | | |
| mannitol | 117.2 | | |
| mais starch | 9.94 | | |
| magnesium stearate | 2.82 | | |

The amounts are indicated in mg.

What is claimed is:

1. Method of treating peripheral arteriopathies in phase III or IV according to the Fontaine classification in a patient in need of such treatment, said method comprising administering to said patient a therapeautically effective amount of defibrotide.

2. Method of treating peripheral arteriopathies in phase III according to the Fontaine classification in a patient in need of such treatment, said method comprising administering to said patient a therapeautically effective amount of defibrotide.

3. Method according to claim 2, wherein said patient is suffering from Buerger's disease.

4. Method according to claim 2, wherein the peripheral arteriopathy is an obliterating arteriopathy of the limbs.

5. Method according to claim 2, wherein said patient is suffering from atherosclerosis.

6. Method according to claim 5, wherein said defibrotide is administered intravenously.

7. Method according to claim 2, wherein said defibrotide is injected intramuscularly.

8. Method according to claim 2, wherein said defibrotide is administered orally.

9. Method according to claim 2, wherein the amount of said defibrotide administered per day is about 6 to about 12 mg per kg of body weight of the patient.

10. Method according to claim 2, wherein about 400 to about 800 mg of defibrotide are administered to said patient per day.

* * * * *